(12) United States Patent
Casterlin

(10) Patent No.: US 6,915,919 B2
(45) Date of Patent: Jul. 12, 2005

(54) CONTAINER CLOSURE CAP WITH SELF-SEALING SLOT

(75) Inventor: Douglas Casterlin, Kinderhook, NY (US)

(73) Assignee: American Bio Medica Corporation, Kinderhook, NY (US)

( * ) Notice: Subject to any disclaimer, the term of this patent is extended or adjusted under 35 U.S.C. 154(b) by 210 days.

(21) Appl. No.: 10/300,627

(22) Filed: Nov. 21, 2002

(65) Prior Publication Data
US 2004/0099628 A1 May 27, 2004

(51) Int. Cl.⁷ ................................................. B65D 39/00
(52) U.S. Cl. .................. 215/247; 220/203.14; 436/518
(58) Field of Search ................... 215/247, 228, 215/246, 248; 220/203.14–203.18; 436/518; 422/102; 600/574

(56) References Cited

U.S. PATENT DOCUMENTS

| | | | | |
|---|---|---|---|---|
| 5,302,348 A | * | 4/1994 | Cusack et al. ................. 422/73 |
| 5,439,143 A | * | 8/1995 | Brown et al. ............. 222/185.1 |
| 5,505,905 A | * | 4/1996 | Corby et al. ................. 422/102 |
| 5,571,667 A | * | 11/1996 | Chu et al. ........................ 435/5 |
| 5,957,898 A | * | 9/1999 | Jepson et al. ................ 604/256 |
| 5,976,895 A | * | 11/1999 | Cipkowski ................... 436/518 |
| 6,419,825 B1 | * | 7/2002 | Hahmann et al. ........... 210/232 |
| 6,669,908 B2 | * | 12/2003 | Weyker et al. ................ 422/58 |

* cited by examiner

Primary Examiner—Lien M. Ngo
(74) Attorney, Agent, or Firm—Edmund M. Jaskiewicz

(57) ABSTRACT

A container for retaining a liquid sample to be tested is closed by a removable closure cap having a slot therein to receive a flat rectangular panel test card member inserted through the slot into the container. A flexible resilient member is mounted adjoining to the closure cap slot and has a slit therein with abutting edges through which the test card is passed. After the test card has been withdrawn, the abutting edges contract to their normally closed position to prevent the leakage of any liquid through the slot when the container is being handled. During withdrawal of the test card through the slot the abutting edges wipe excess liquid sample from the test card.

16 Claims, 5 Drawing Sheets

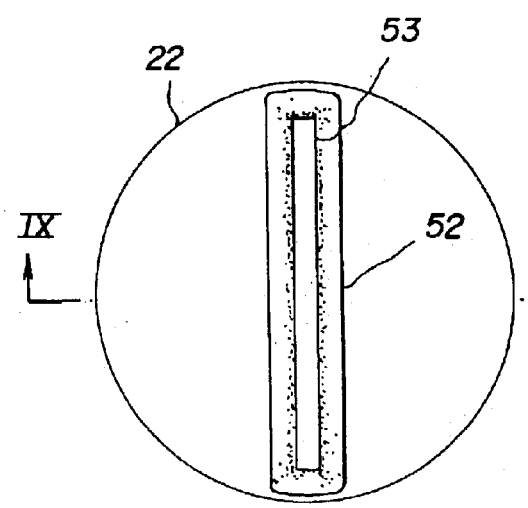
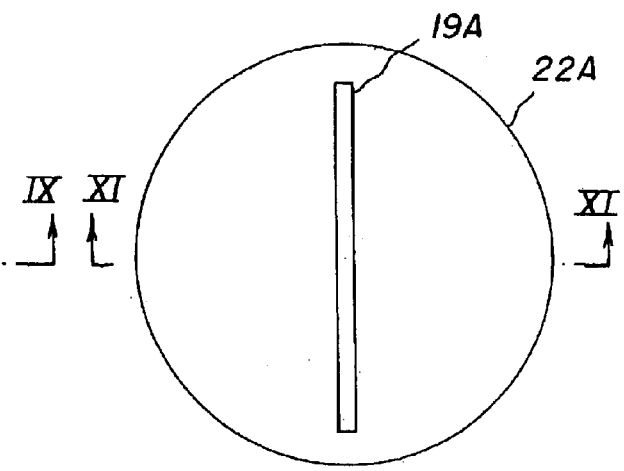
FIG. 8    FIG. 10
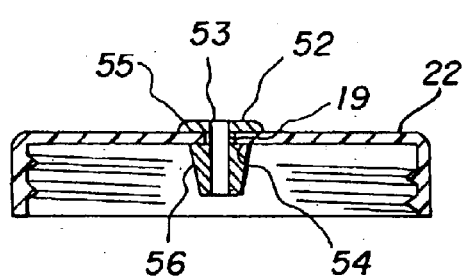
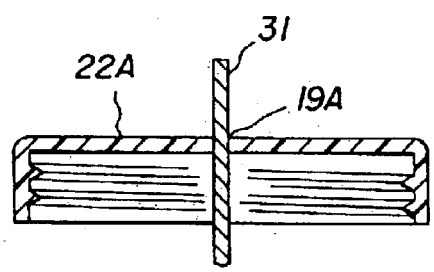
FIG. 9    FIG. 11

FIG. 12
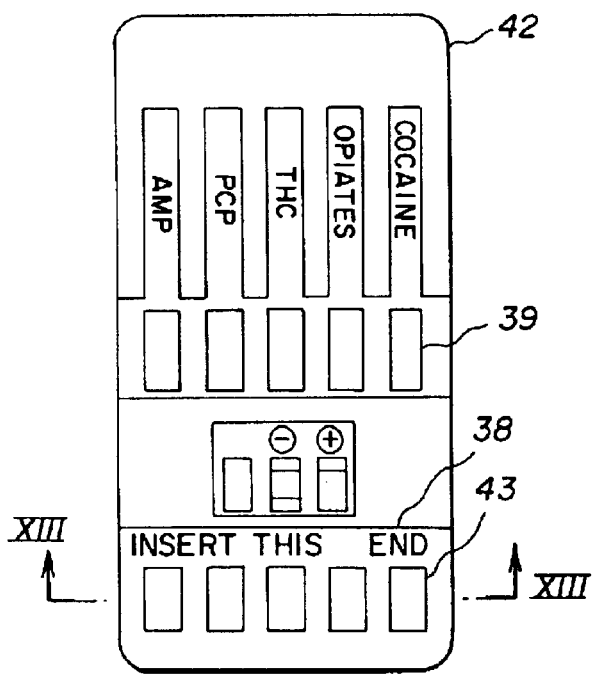
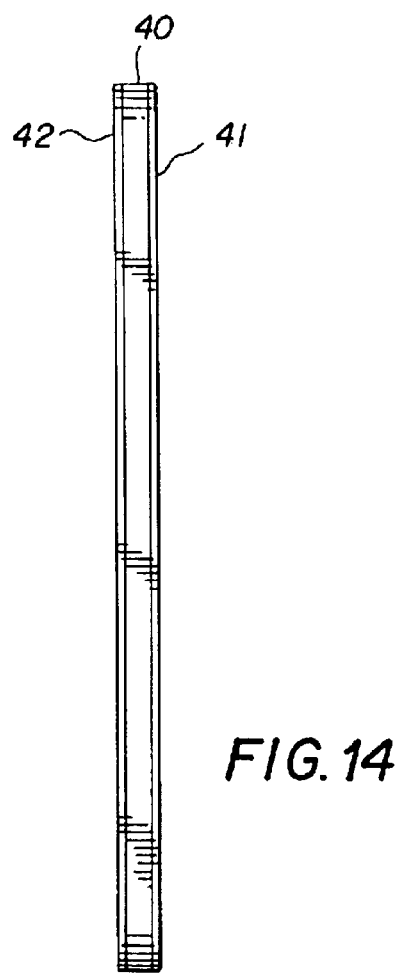
FIG. 14
FIG. 13
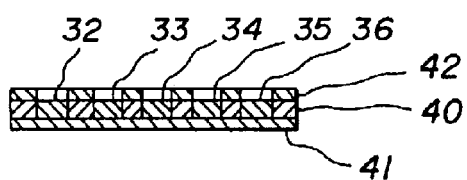

CONTAINER CLOSURE CAP WITH SELF-SEALING SLOT

BACKGROUND OF THE INVENTION

The present invention relates to a test kit for the collection and testing of urine samples for drugs of abuse having a cup-like container and a test card for indicating visually the presence of a particular drug of abuse, more particularly, to a closure cap for such a container having a self-sealing slot through which the test card is passed.

The increased availability and use of drugs of abuse by the general population has caused employers, governmental agencies, sports groups and other organizations to utilize drug screening both as a condition of employment and in order to maintain safety in the workplace. Typical drug screening tests are performed for the purpose of quickly identifying on a qualitative basis the presence of drugs in a body fluid which may be urine. A complete analysis of the sample may then be carried out in a laboratory only if the preliminary screening results are not negative. Increasingly, such drug screening procedures are taking place on site or at the workplace and are generally carried out by testing personnel who are usually not technically trained, such as laboratory technicians. It is thus important that the drug screening procedure be simple but yet reliable. Further, the test apparatus must be such so as to enable the testing personnel to avoid all contact with the fluid specimen which is being tested.

Various forms of devices have been proposed for the collection and taking of body fluids, such as urine, which have proved to be cumbersome in operation since they involve a number of separate steps. Initially, the sample was collected and several steps were then required to transfer the urine sample to an analysis device. This multiple step procedure required the manual handling of the specimen through various devices and the use of such transfer devices inevitably caused spills which could result in contamination to the tester and surroundings. In addition, non technical personnel who perform the screening tests on urine samples objected to coming into any kind of contact with the urine sample and even the handling of the sample itself.

One such testing device comprised a cup-like container which may be transparent for retaining a urine sample to be tested. The open top of the container has a removable closure cap and there is a diametrical slot in the cap. The slot is of such a size as to readily accommodate a test card which has a plurality of immunoassay test strips mounted thereon in parallel on one or both sides and each test strip is responsive to a particular drug of abuse. The test card is insertable through the slot so as to immerse one end in the urine sample to a predetermined depth whereby the visual results of each test strip may be seen through a transparent wall of the container or above the closure cap without removing the test card from the container so as to indicate the presence or absence of a particular drug of abuse in the urine sample. If the sample should test "positive" to indicate the presence of a drug in the urine, it is then necessary to send the sample to a certified laboratory for confirmatory testing. For this purpose, a second closure cap which is solid, i.e., without a slot, was provided which was threaded onto the open end of the cup-like container. The test card is removed from the container, the slotted cap is removed and replaced by the solid closure cap which is threaded on to close the container and the container is then ready for shipment to a laboratory.

However, prior to replacing the slotted cap with the solid cap it was found that occasionally the cup was accidentally tipped over while the card was still in the cup or after the card had been removed from the cup. In such an event, the liquid sample could and did spill from the slot in the cup onto surrounding surfaces and even into contact with the testing personnel. Thus, such open specimen containers posed a risk of contamination of the sample or specimens, contamination of the laboratory environment, loss of specimens through accidental spillage, and possible infection of personnel. It was therefore apparent that the handling and processing of urine and other similar liquid medical specimens should involve a minimum of opening and closing the specimen containers at the testing locations.

DESCRIPTION OF RELATED ART

In U.S. Pat. No. 5,904,677 there is disclosed a specimen cup having an opening in its cap which is covered by a self-sealing membrane which can be penetrated by a syringe. Upon withdrawal of the syringe, the puncture in the membrane is self-sealing.

U.S. Pat. No. 6,030,582 discloses a self-resealing container cap in which there is an opening covered by a septum of an elastomeric material which can be punctured by a blunt tip of an instrument such as a pipette. Upon withdrawal of the pipette the puncture is self-sealed.

In U.S. Pat. No. 3,315,402, there is disclosed a live bait container covered by a diaphragm with an elongated slit therein which can be pressed open by hand pressure. Upon withdrawal of the hand the slit is self-closing but is not self-sealing.

Other self-sealing container closures each having an opening to accommodate sharp or blunt pointed instruments are shown in U.S. Pat. Nos. 5,111,946; 2,436,291 and 6,241,113.

None of the prior art suggests or discloses providing a self-sealing slot in a container wherein a thin card is passed through the slot into the container and the slot is self-sealing during withdrawal of-the card through the slot and after the card has been withdrawn.

SUMMARY OF THE INVENTION

It is therefore the principal object of the present invention to provide a novel and improved slotted self-sealing closure cap for a container for the testing of fluid samples or specimens.

It is another object of the present invention to provide a self-sealing elongated slot which can accommodate a rectangular panel test card member and which sealingly closes after the test card has been withdrawn.

It is a further object of the present invention to provide such a container closure cap which has an elongated slot therein through which can be inserted a thin flat panel-like member and the slot is self-sealing during withdrawal of the card through the slot and after the card has been withdrawn.

The objects of the present invention are achieved and the disadvantages of the prior art are eliminated by the container closure cap having a self-sealing slot according to the present invention which may comprise a closure cap positionable over the open top of a container for retaining a liquid sample to be tested by a flat rectangular panel test card member inserted and withdrawn through a slot in the closure cap. The slot is elongated to accommodate a test card which is inserted into the container to contact the liquid sample to be tested. Adjoining the closure cap slot is a resilient material in which is formed a self-sealing slit having abutting edges and disposed substantially centrally of the cap slot.

The abutting edges of the slit are normally closed but are expansible responsive to-pressure exerted by a flat panel-like member inserted therethrough and the slit edges maintain contact with the test card member so as to wipe the faces and edges of the test card when it is being withdrawn from the container. When the panel member has been withdrawn from the container the edges of the slit are contractible to the normally closed position and in this position are self-sealing against the leakage of sample liquid from the container.

When using a transparent container and the test card is inserted into the container to contact the fluid specimen the results of the test can be viewed through the transparent wall of the container and it is not necessary to withdraw the card from the container. After many tests, particularly when the results are negative, the container and test card inserted into the container can be discarded as a unit. In this instance it is desirable that the slot sealingly engage the test card so that there is no leakage of fluid sample through the slot around the test card inserted therein.

In one embodiment of the invention, a disc of a resilient foam like material is attached to the underside of the closure cap and a slit is formed in this material to accommodate the test card.

In a modification of the invention an elastomeric material is molded onto the edges of the slot in the closure cap to form a thin membrane in the center of the slot and this membrane is provided with a thin slit to accommodate the card. The membrane may also be made in such a manner so as to be penetrated by the edge of the test card to in effect, form the slit.

In another modification an elastomeric insert having a slit therein is inserted into the slot of the closure cap.

In a further modification the closure cap itself is made of an elastomeric material and the slot in the cap closely receives the test card so as to be sealingly engaged with the card while the card is within the slot. This slot may also be provided with a membrane which sealingly closes the entire slot after the card has been withdrawn therefrom.

BRIEF DESCRIPTION OF THE DRAWINGS

Other objects and advantages of the present invention will be apparent upon reference to the accompanying description when taken into conjunction with the following drawings, which are exemplary, wherein;

FIG. 8 is a top plan view of the closure cap of FIG. 3 but having a further modification in the slot structure which is in the form of an insert;

FIG. 9 is a sectional view taken along the line IX—IX of FIG. 8;

FIG. 10 is a top plan view of the closure cap shown in FIG. 3 but showing a modified cap in which the cap is made of an elastomeric material;

FIG. 11 is a sectional view taken along the line XI—XI of FIG. 10;

FIG. 12 is a plan view of the test card in the test kit of the present invention;

FIG. 13 is a sectional view taken along the line XIII—XIII of FIG. 12;

FIG. 14 is a side elevational view of the test card shown in FIG. 12;

DETAILED DESCRIPTION OF THE INVENTION

Figure 1:
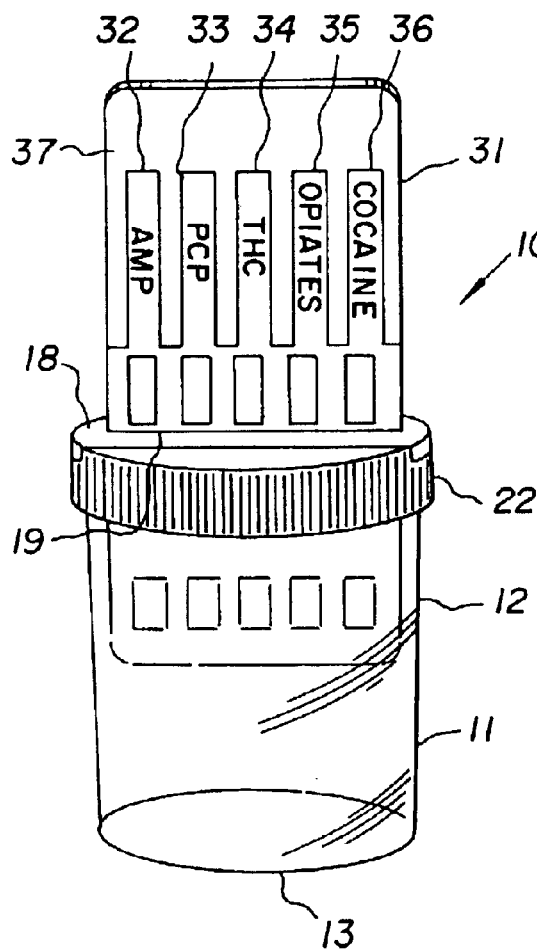
FIG. 1 is a perspective view of the drug abuse test kit according to the present invention generally showing the cup-like container and the test card being partially inserted to the testing position in the container through the slot in the closure cap.
Figure 2:
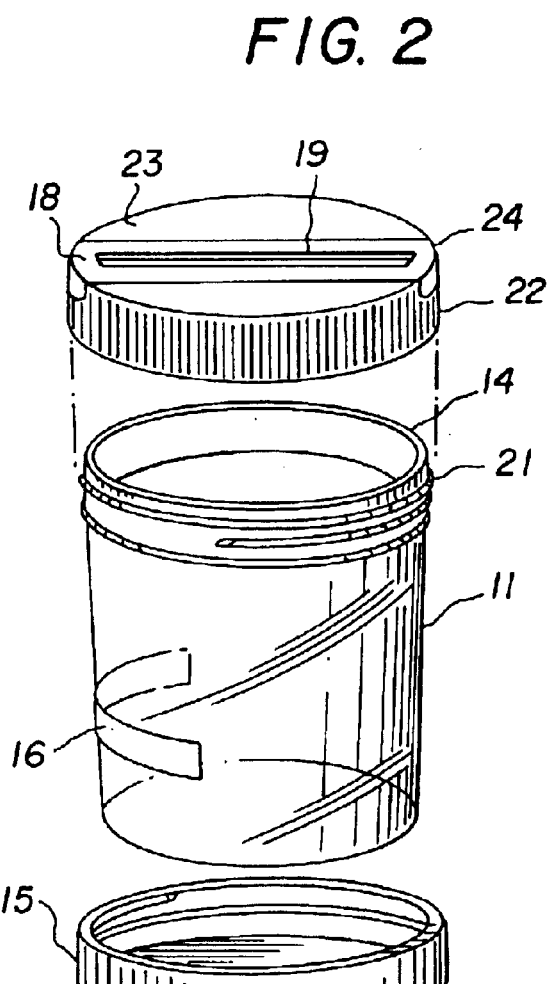
FIG. 2 is an exploded perspective view of the container for collecting and testing a fluid sample and generally showing the container, a closure cap having a slot covered with a removable adhesive seal and a second solid closure cap.

As may be seen in FIGS. 1 and 2, a drug abuse test kit incorporating the present invention is indicated generally at 10 and comprises a cup-like transparent test container or cup 11 made of a plastic material such as styrene and having a cylindrical sidewall 12, a closed bottom 13 and an open top 14. The cylindrical wall 12 may have a slight taper or be straight.

Figures 5, 7:
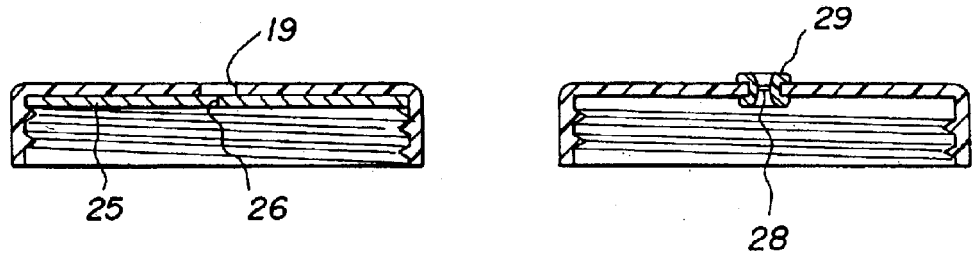
FIG. 5 is a sectional view taken along the line V—V of FIG. 4.
FIG. 7 is a sectional view taken along the line VII—VII of FIG. 6.
Figure 15:
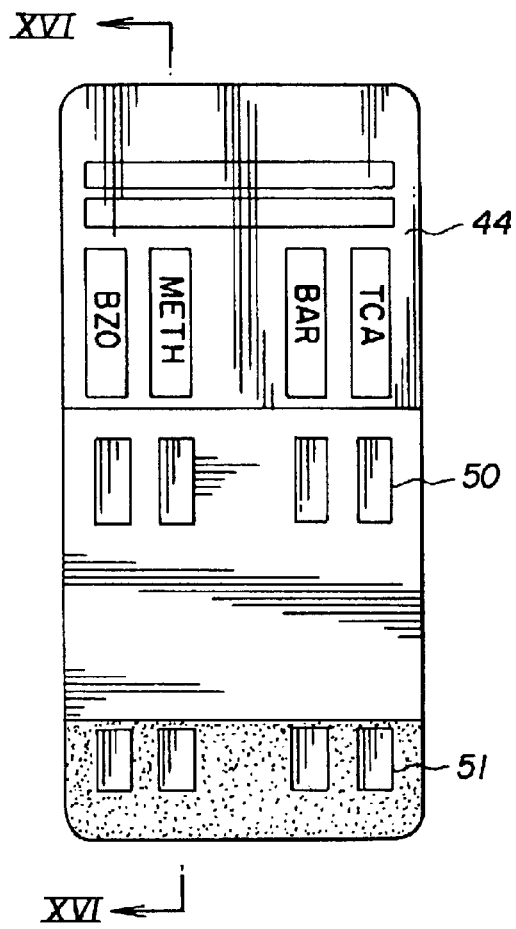
FIG. 15 is a plan view of a modification of the test card shown in FIG. 12 which is also used in the test kit of the present invention.
Figures 16, 17:
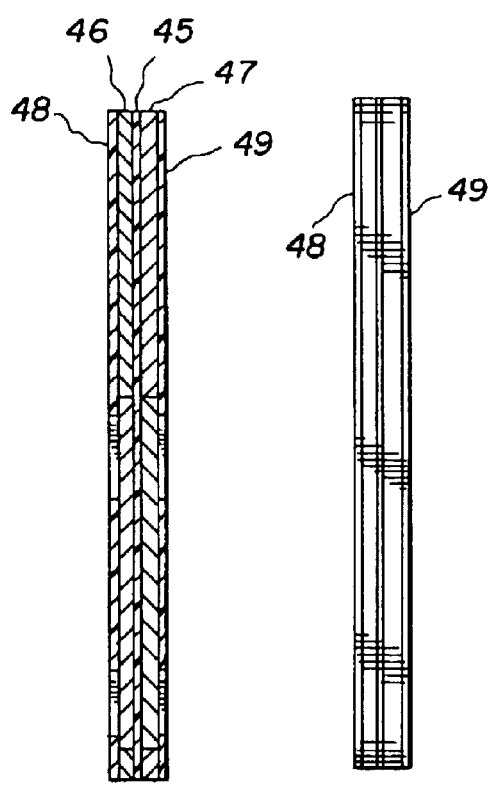
FIG. 16 is a sectional view taken along the line XVI—XVI of FIG. 15.
FIG. 17 is a side elevational view of the test card shown in FIG. 15.

The open top end 14 of the test cup 11 is provided with external threads 21 upon which is seated an outer relatively rigid closure cover or cap 22 made of an inelastic plastic material such as polypropylene or polyethylene and provided with corresponding internal threads as may be seen in FIGS. 5 and 7. The cover 22 has a circular top surface 23 from the periphery of which depends a cylindrical wall 24 on the outer surface of which are provided the internal threads. The cover surface 23 has a diametrical slot 19 therein shaped to accommodate a test card as described subsequently. There is also provided a solid cover or cap 15 which is similar in size and shape to the cover 22 but is solid or unslotted so that the covers 15 and 22 may be interchangeable on the open end 14 of the test cup 11. During any shipment of the test kit, the cover 15 is generally fitted on the bottom of the test cup. A temperature strip 16 may be mounted on the bottom side wall of the test cup so as to be responsive to the temperature of the test sample within the test cup. A readily removable adhesive sealing strip 18 may be placed over the slot 19 in the closure cap 22 to prevent the entry of any foreign matter into the container prior to its usage in testing.

Figure 3:
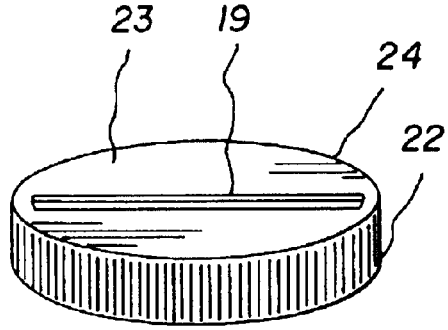
FIG. 3 is a perspective view of the container closure cap having a slot in its top surface.
Figures 4, 6:
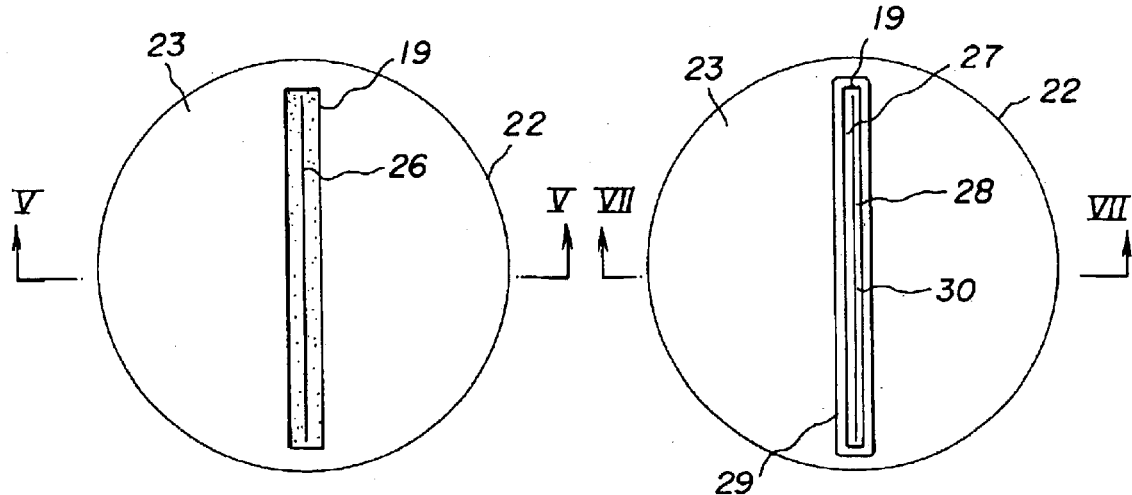
FIG. 4 is a top plan view of the closure cap in FIG. 3.
FIG. 6 is a top plan view of the closure cap of FIG. 3 but showing a further modification of the slit structure in the cap.

One embodiment of the present invention is shown in FIGS. 3–5 in which a disk of a cross-linked polyethlene foam is attached to the underside of the cap top surface 23. Attachment may be made by a pair of adhesive strips parallel to and on each side of the closure cap slot 19. The disk is provided with a diametrical slit 26 positioned so as to be central of the cap slot 19. The thickness of the disk 25 is substantially equal to the thickness of a test card which is of the order of $\frac{1}{8}$ inches thick. Such a disk was provided by the Atlantic Gasket Corporation of Philadelphia, Pa.

The abutting edges of the slit 26 are so narrow being of the order of 0.016 inches wide, that the abutting edges of the slit 26 are normally in contact with each other so as to close the slit.

In the modification illustrated in FIGS. 6 and 7, a slit 27 is formed in a thermoplastic elastomer membrane 28 which extends across the slot 19 between portions of the elastomer 29 which are molded onto all edges of the slot 19 as may be more clearly shown in FIG. 7. Such an elastomer is available from Advanced Elastomer Systems of Brussels, Belgium.

When the slit 27 is formed, the edges of the membrane on both sides of the slit form-wiping edges 30. These edges brush against the test card as it is withdrawn from the slot to wipe liquid therefrom. In this modification also, the slot is so thin and narrow that its edges are abutting in its normally closed position.

As a further modification, the elastomer may be molded onto the edges of the slot to form a solid membrane across the slot 19. However, this membrane is such that it can be penetrated by the edge of a rectangular panel test card member. In this modification, the wiping flaps 30 will be formed only after the membrane has been penetrated by the test card to form, in effect, the slit 27.

Another modification of the slot-structure is illustrated in FIGS. 8 and 9 in which an insert 52 made of a thermal plastic elastomer is inserted into the slot 19 of the closure cap 22. The insert 52 is an elongated member having a central slit 53 and extending peripherally around the insert 52 and perpendicular to the plane of the slit 53 is a groove 54 which divides the insert into an upper portion 55 and a lower portion 56. The lower portion 56 has a substantially V-shape as shown in FIG. 9 to facilitate insertion into and passage through the slot 19 of the cap 22. The insert 52 is formed of such a resilient and elastic material that the slit 53 closely accommodates a test card inserted therethrough and the edges of the slit 53 wipe along the faces and edges of the test card so as to form a seal with the test card when the test card is within the slit 53. This sealing with the test card may be further enhanced by providing in the slit 53 a thin membrane having a very narrow slit therein such that the edges of the membrane slit are pushed apart by a test card inserted therethrough. When a test card has been withdrawn from the container the edges of the membrane will return to their original abutting or closed positions and thus provide sealing of the container after the test card has been removed. The structure of such a membrane is similar to the elastomer membrane 28 shown in the closure cap illustrated in FIGS. 6 and 7.

FIGS. 10 and 11 illustrate a still further modification in which the closure cap 22A is made of a thermoplastic elastomer membrane and is provided with a slot 19A which closely accommodates a test card inserted therethrough. The edges of the slot 19A will wipe against the faces and edges of a test card 31 inserted into the slot 19A so as to form a seal with the test card while the test card remains in the slot 19A.

In this modification also a thin membrane with a slit may be provided or formed within the slot 19A of the closure cap.

The test kit as shown in FIG. 1 comprises a test card 31 which will indicate the presence or absence of any one of five different drugs of abuse and is shown in further detail in FIGS. 8–10. The test card is of the multiple drug type in which test strips 32, 33, 34, 35 and 36 for five different drugs of abuse are mounted on a face 37 of the test card. These test strips are spaced apart in parallel on the test card and indicate the presence or absence of the following specific drugs of abuse: Amphetamines (AMP), PCP, marijuana (THC), opiates and cocaine. Such test strips are made by American Bio Medica Corporation of Kinderhook, N.Y. and are characterized as immunoassay strips and employ colloidal gold chemistry. The test strips are submerged up to a maximum line indicated at 38 in FIG. 8 and the results of the test are read in a test area indicated at 39. A blue line in the test area indicates positive or the presence of a particular drug in the test sample.

The test card as shown in FIGS. 8–10 comprises a central ply 40 of styrene and both faces of the central ply are covered a bottom ply 41 and a top ply 42. Slots are provided in the central ply 40 to accommodate the test strips as shown in FIG. 9. The top and bottom plys may be of a thin vinyl sheet or cardboard coated with plastic. The top ply 42 is provided with a plurality of test windows 39 through which the test results as indicated by the test strips can be seen. At the lower end of the test card are provided sample openings through which the liquid test specimen is able to contact the absorbant or sample portions of the test strips.

In FIGS. 11–13 there is shown a modification of the test card in which test strips are mounted on both sides of the test card so that up to a total of nine different test strips are mounted so as to be able to test for nine different drugs of abuse in the same specimen or sample. This modified test card 44 has a central divider layer 45 and on both sides of this layer are mounted polystyrene plys 46 and 47 in which the immunoassay test strips are mounted as previously described. The styrene plys are covered by front and back plys 48 and 49. Each of which are provided with viewing windows 50 and sample receiving windows 51 again as previously described. When the present invention is to be used, the person being tested must first provide a sufficient quantity of a urine specimen into the test cup 11. The test cup is then closed by threading the cap 22 on top of the test cup. The slot 19 on the cap of the test cup is provided with a readily removable adhesive sealing strip 18. When the container with the test specimen is brought to the person conducting the test, the protective strip 18 is removed and a multiple drug test card such as 31 or 44 is inserted into the cap slot 19 through the slit 26 or 27 within the slot 19 so that the bottom of the test card rests upon the bottom of the test cup. The test card then remains in place for at least three minutes and the results of the test can be read on each individual test strip through a transparent wall of the container. Or, if a container of lower height is used, the results of the tests are viewed above the closure cap.

When the test results are read on the test card, the test has been completed and the test card must now be withdrawn from the test cup. As the card is withdrawn, the abutting edges of the slit 26 or 27 will wipe liquid from the test card during the withdrawal thereof and when the card has been completely withdrawn the abutting edges of the slit will close to self-seal the slot in the closure cap. Thus, even if the test cup should be inadvertently tipped over or knocked onto the floor from the laboratory table there will be no significant leakage of liquid from the container. As a result, the likelihood of any contamination of the surrounding testing area or of personnel conducting the testing is avoided.

Each of the test strips in the test cards is a one-step immunoassay in which a specially labled drug, (drug conjugate) competes with a drug which may be present in the sample for the limited number of binding sites on an antibody. The test strip consists of a membrane strip onto which a drug conjugate has been immobilized. A colloidal gold-antibody complex is dried at one end of the membrane. In the absence of any drug in the urine sample, the colloidal gold-antibody complex moves with the urine sample by capillary action to contact the immobolized drug conjugate. An antibody-antigen reaction occurs forming a visible line in the test area. Thus, the formation of a visible line in the test area occurs when the test is negative for the drug.

Thus, it can be seen that the self-sealing slotted closure cap of a test container greatly facilitates the handling of such test containers since there is virtually no likelihood of spillage if the test container is mishandled. Further, the wiping action of the self-sealing slot during withdrawal of the test card from the container results in a test card which has a minimum of the liquid sample adhering to it.

It will be understood that this invention is susceptible to modification in order to adapt it to different usages and conditions, and accordingly, it is desired to comprehend such modifications within this invention as may fall within the scope of the appended claims.

What is claimed is:

1. A closure cap positionable over the open top of a container for retaining a liquid sample to be tested by a test card inserted into the container, said closure cap made of a relatively inelastic material and having an elongated slot therein to accommodate a thin flat rectangular panel test card member inserted there-through into the container to contact the liquid sample to be tested, means mounted on said cap and adjoining said slot for defining a self-sealing slit having abutting edges and disposed substantially centrally of said slot, said slit abutting edges being normally closed but expansible responsive to pressure exerted by a panel test card inserted therethrough and maintaining contact with said test card so as to wipe the faces and edges of said test card to form a seal with the card when the card is within said slot.

2. A closure cap as claimed in claim 1 wherein said means comprises a sheet of resilient material disposed on the underside of the closure cap.

3. A closure cap as claimed in claim 2 wherein said sheet comprises a disc attached on the underside of said closure cap.

4. A closure cap as claimed in claim 3 wherein said disk comprises a polyester foam material.

5. A closure cap as claimed in claim 1 wherein said means comprises a resilient membrane extending between the edges of said slot.

6. A closure cap as claimed in claim 5 wherein said resilient membrane is morded onto the edges of said slot.

7. A closure cap as claimed in claim 1 wherein said container has a circular cross section, said slot in the cap has a length substantially equal to the inner diameter of said container.

8. A closure cap as claimed in claim 6 wherein said membrane comprises an elastomer material which is penetrated by an edge of the panel member test card to form the slit which is self-sealing.

9. A closure cap as claimed in claim 6 wherein said membrane has a central portion capable of being penetrated by the edge of a said test card to define a self-sealing slit.

10. A closure cap as claimed in claim 6 wherein said membrane comprises a central portion having a thin slit therein to receive an edge of a panel member test card.

11. A closure cap as claimed in claim 1 wherein said slit abutting edges are contractible to the normally closed position when said test card panel member has been withdrawn from the container to be self-sealing against leakage of sample liquid.

12. A closure cap as claimed in claim 1 wherein said means for defining a self-sealing slit comprises an elongated member having top and bottom faces and a central elongated slit therethrough to closely accommodate a panel test card and further having a peripheral groove in a plane parallel to said top and bottom faces, said groove receiving therein the edges of said cap slot such that top and bottom portions of said elongated member contact the top and bottom faces of the closure cap surrounding said slot.

13. A closure cap as claimed in claim 12 wherein said elongated member has a thin elastomer resilient membrane extending across said elongated slit, said membrane being penetrable by an edge of the panel test card to form a slit therein which is self-sealing.

14. A closure cap as claimed in claim 12 wherein said elongated member has a thin elastomer resilient membrane extending across said elongated slit, said membrane having a slit therethrough the edges of which will wipe the faces and edges of a test card being passed therethrough.

15. A process for forming a self-sealing slot in a container closure cap comprising the steps of depositing a thermoplastic elastomer material on the edges of a pre-existing slot in the closure cap in such a manner as to define beads on the upper and lower surfaces of the edges of the slot and a thin resilient membrane extending from the beads over the slot, and forming in the thin membrane a slit of such a width that the edges of the slit are abutting to sealingly close the slit.

16. A process for forming a self-sealing slot in a container closure cap comprising the steps of depositing a thermoplastic elastomer material on the edges of a pre-existing slot in a closure cap in such a manner as to define beads on the upper and lower surfaces of the edges of the slot and a thin resilient membrane extending from the beads over the slot, the resilient membrane being of such a thickness as to permit penetration thereof by an edge of a thin flat rectangular panel member to define an elongated slit the edges of which are sufficiently resilient and near to each other to sealingly close the slit after removal of the panel member from the slit.

* * * * *